United States Patent [19]
Patterson et al.

[11] Patent Number: 5,840,478
[45] Date of Patent: Nov. 24, 1998

[54] METHOD OF DETECTING AMPLIFIED NUCLEIC SEQUENCES IN CELLS BY FLOW CYTOMETRY

[75] Inventors: Bruce Patterson; Michelle Till, both of Chicago; Steven Wolinsky, Glencoe, all of Ill.

[73] Assignee: Northwestern University, Evanston, Ill.

[21] Appl. No.: 245,530

[22] Filed: May 18, 1994

Related U.S. Application Data

[63] Continuation of Ser. No. 901,702, Jun. 19, 1992, abandoned.
[51] Int. Cl.[6] .............................. C12Q 1/70; C12Q 1/68; C12P 19/34
[52] U.S. Cl. .................................. 435/5; 135/6; 135/91.2; 935/78
[58] Field of Search .................................. 435/5, 6, 91.1, 435/91.2, 91.51

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,770,992 | 9/1988 | Van den Engh et al. | 435/6 |
| 5,436,144 | 7/1995 | Stewart et al. | 435/91.2 |
| 5,480,783 | 1/1996 | Haff | 435/91.2 |

OTHER PUBLICATIONS

Komminoth, et al. (1992) Diagnostic Molecular Biology 1:85–87 Jun.

Timm, E.A, et al. Genotyping Cells by Flow Cytometry Using PCR Techniques. Abstracts for the XIV International Meeting of the Society for Analytical Cytology, Mar. 18–23, 1990. (Abstract 481B–p.79).

Costa Taveira, N., et al. Detection of HIV1 proviral DNA by PCR and hybridization with digoxigenin labelled probes. Int. Con. AIDS (Jun 20, 199)6:157 (Abstract No. F.A. 327).

Seibl, R., et al Non–Radioactive Labelling and Detection of Nucleic Acids. III. Applications of the Digoxigenin System. Biol. Chem. Hoppe–Seyler (Oct. 1990) 371:939–951.

Meyer et al. DNA Flow Cytometry of Breast Carcinoma After Acetic–Acid Fixation, Cell. Tissue Kinet. (1984) 17:184–197. (Abstract).

Tournier et al. Detection of Albumith mRNAs in Rat Liver by Insitu Hybridization: Usefulness of Paraffin Embedding and Comparison of Various Fixation Procedures. J.Histochem Cytochem (Apr. 1987) 35:453–459 (Abstract).

P. H. Hinderling, Kinetics of Partitioning and Binding of Digoxin and Its Analogues in the Sub Compartments of Blood. J.Pharm Sci (1984)73:1042–1052.

Basgasra et al., Detection of Human Immunodeficiency Virus Type I Provirus in Monocuclear Cells by In Situ Polymerase Chain Reaction, N. Eng. J. Med. 326, 1385 (1992).

Bauman et al., Flow Cytometric Detection of Ribosomal RNA in Suspended Cells by Fluorescent In Situ Hybridization[1,2], *Cytometry* 9:515–524 (1988).

Dudin et al., A Method for Nucei Acid Hybridization to Isolated Chromosomes in Suspension, *Hum. Genet* 76:190–292 (1987).

(List continued on next page.)

*Primary Examiner*—Stephanie W. Zitomer
*Assistant Examiner*—Amy Atzel, Ph.D.
*Attorney, Agent, or Firm*—Dressler, Rockey, Milnamow & Katz, Ltd.

[57] ABSTRACT

The field of this invention is the detection and isolation of specific amplified DNA sequences by flow cytometry. More particularly, this invention relates to the detection of these specific amplified DNA sequences in cells so as to allow quantitation of viral burden of patients infected with a virus. The method is particularly adapted to detection of HIV-1 proviral DNA sequences and the assessment of activity of the virus in a cell.

16 Claims, 3 Drawing Sheets

OTHER PUBLICATIONS

Folks et al., Biological and Biochemical Characterization of a Cloned LEU–3 Cell Surviving Infection with the Acquired Immune Deficiency Syndrome Retrovirus, *J. Exp. Med.* 164:280–290 (1986).

Harper et al., Detection of Lymphocytes Expressing Human T–lymphotropic virus Type III in Lymph Nodes and Peripheral Blood from Infected Individuals by in situ hybridization, *Proc. Natl. Acad. Sci USA* 83;772–776 (1986).

Hsia et al., Human Immunodeficiency virus DNA is Present in a High Percentage of $CD4^{30}$ Lymphocytes of Seropositive Individuals, *J. Infect. Dis.* 164:470–475 (1991).

Mullis et al., [21]Specific Synthesis of DNA in Vitro via a Polymerase–Catalyzed Chain Reaction,*Methods of Enzymo.* 155:335–350 (1987).

Ou et al., DNA Amplification for Direct Detection of HIV–1 in DNA of Peripheral Blood Mononuclear Cells, *Science* 238:295–297 (1988).

Pinkel et al., Cytogenetic Analysis by In Situ Hybridization with Fluorescently Labeled Nucleic Acid Probes, *Cold Spring Harbor Symposia on Quantative Bio.* LI:151–157 (1986).

Saiki et al., Enzymatic Amplification of β–Globin Genomic Sequences and Restriction Site Analysis for Diagnosis of Sickle Cell Anemia, *Science* 230:1350–1354 (1985).

Saiki et al., Primer–Directed Enzymatic Amplification of DNA with a Thermostable DNA Polymerase, *Science* 239:487–491 (1988).

Schnittman et al., The Reservoir for HIV–1 in Human Peripheral Blood Is a T Cell That Maintains Expression of CD4, *Science* 245:305–308 (1989).

Schnittman et al., Increasing Viral Burden in CD4+ T Cells from Patients with Human Immunodeficiency Virus (HIV) Infection Reflects Rapidly Progressive Immunosuppression and Clinical Disease, *Ann. Intern. Med.* 113:438–443 (1990).

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 32 base pairs
      ( B ) TYPE: nucleic acid
      ( C ) STRANDEDNESS: unknown
      ( D ) TOPOLOGY: unknown ( i i ) MOLECULE TYPE: DNA (genomic)

( x i ) SEQUENCE DESCRIPTION: SEQ ID NO:1:

GCGAATTCAT GGAGCCAGTA GATCCTAGAC TA　　　　　　　　　　　　　　　　　　　　　　　　　3 2

( 2 ) INFORMATION FOR SEQ ID NO:2:

( i ) SEQUENCE CHARACTERISTICS:
      ( A ) LENGTH: 32 base pairs
      ( B ) TYPE: nucleic acid
      ( C ) STRANDEDNESS: unknown -continued (D) TOPOLOGY: unknown (ii) MOLECULE TYPE: DNA (genomic)

(xi) SEQUENCE DESCRIPTION: SEQ ID NO:2:

GCGAATTCAT GGATCCAGTA GATCCTAGAC TA    32

(2) INFORMATION FOR SEQ ID NO:3:

(i) SEQUENCE CHARACTERISTICS:
(A) LENGTH: 36 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:3:

GCTCTAGACT ATCTGTCCCC TCAGCTACTG CTATGG    36

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:4:

TTCTCTATCA AAGCAACCCA CCTCCCAATC    30

METHOD OF DETECTING AMPLIFIED NUCLEIC SEQUENCES IN CELLS BY FLOW CYTOMETRY

This application is a continuation of application Ser. No. 07/901,702, filed Jun. 19, 1992, now abandoned.

FIELD OF THE INVENTION

The field of this invention is the detection of amplified nucleic acid sequences by flow cytometry. More particularly, this invention relates to the detection of these amplified nucleic acid sequences in cells, so as to allow quantitation of viral burden of patients infected with a virus. Additionally this invention will allow identification of aberrant cellular genes related to a genotypic carrier state or related to malignancy and of fetal cells in the maternal circulation that arise during maternal/fetal exchange.

BACKGROUND OF THE INVENTION

Detection of viral nucleic acids in specimens comprising body fluids or tissues can be difficult because of the small quantity of viral DNA present in the specimen and/or because of the presence of other interfering materials, including DNA from a different source. These limitations may be overcome by employing the analytic method referred to as the polymerase chain reaction (PCR) technique. By this technique, selective enrichment of a specific DNA sequence can be achieved by exponential amplification of the target sequence. [See Mullis, et al., *Methods Enzymo.*, 155, 335 (1987); and Saiki, et al., *Science,* 230, 1350 (1985)].

To facilitate PCR amplification, pairs of oligonucleotide primers may be employed as described in U.S. Pat. Nos. 4,683,202 and 4,683,195. The primers are designed to hybridize with sequences that flank the target DNA. Following in vitro amplification, the amplified target sequence is detected by a hybridizing, target-specific probe. For example, this analytical procedure has been used for direct detection of HIV-1 (AIDS virus), as described by Ou, et al., *Science,* 238, 295–297 (Jan. 15, 1988). The amplification cycles are facilitated by using a polymerase which is thermally stable in incubations up to 95° C., as described by Saiki, et al., *Science,* 239, 487–491 (Jan. 29, 1988).

Generally, specific amplified nucleic acids are detected by hybridization with labeled nucleic acid sequences complementary to a region within the amplified nucleic acid. Thus, the whole population of amplified nucleic acids are simultaneously detected.

Other measurement techniques, however, allow the analysis of individual cells. These techniques included microscopy and flow cytometry. Flow cytometry, involves analyzing cells or cellular fractions suspended in a solution that are stained with fluorescent dyes. In flow cytometry, cells are forced in a narrow stream through a path of laser light. The cells pass the laser beam in single file at a rate up to several thousand per second. When cells enter the light, they scatter light or emit fluoresence. As each cell passes through the light source, its optical properties are quantified and stored with this technique. A large number of cells can be measured and characterized individually in a short period of time.

Van den Engh et al., U.S. Pat. No. 4,770,992 show detection of DNA sequences in chromatin by flow cytometry. The method disclosed by Van den Engh et al., however, does not allow for the detection of short target sequences or nucleic acids located in the cytoplasm. To make these assessments an intact cell must be analyzed.

Quantification of viral burden in patients with an infection is relevant for prognostic and therapeutic purposes. For example, several studies have attempted to quantify Human Immunodeficiency Virus (HIV-1) DNA or RNA using coamplification of HIV-1 GAG and HLA-DQ-α [See T. Lee, F. J. Sunzeri, L. H. Tobler, et al.,*Aids* 5, 683 (1991)], quantitative RNA PCR [See L. Q. Zhang, P. Simmonds, C. A. Ludlam, A. J. L. Brown, *Aids* 5, 675 (1991)], and quantitative DNA PCR following cell sorting [See S. M. Schnittman, M. C. Psallidopoulos, H. C. Lane, et al., *Science* 245, 305 (1989)]. In addition, histologic methods such as in situ hybridization using cRNA probes complementary to HIV-1 RNA [See M. E. Harper, L. M. Marselle, R. C. Gallo, F. Wong-Staal, *Proc Natl Acad Sci USA* 83, 772 (1986)] and in situ PCR for HIV-1 proviral DNA [See O. Basgasra, S. P. Hauptman, H. W. Lischner, M. Sachs, R. J. Pomerantz, *N Engl J Med* 326, 1385 (1992)] have been used to directly identify infected peripheral mononuclear cells isolated from patients. Due to the markedly discordant results in these studies only limited insight is gained into the percent of infected cells in HIV-1 patients with estimates ranging anywhere from 10% of cells in symptomatic patients containing HIV-1 DNA [See K. Hsia, S. A. Spector,*J Infect Dis* 164, 470 (1991)] to between 1 in 100 and 1 in 100,000 cells in asymptomatic carriers containing HIV-1 (See S. M. Schnittman, J. J. Greenhouse, M. C. Psallidopoulos, *Ann Intern Med* 113, 438 (1990)]. Additionally, the lack of consistent data confuses interpretations of the role that this determination plays in disease progression and prognosis.

Previous attempts to combine nucleic acid hybridization with flow cytometry have been restricted by target copy number or sequence specificity. Solution hybridization and flow cytometric detection of positively hybridized nuclei has been reported utilizing either total genomic DNA [See G. Dudin, T. Cremer, M. Schardin et al., *Hum Genet* 76, 290 (1987)] or highly repetitive chromosome specific sequences [See D. Pinkel, J. W. Gray, B. Trask, *Cold Spring Harbor Symposia on Quantitative Biology,* Vol. LI., 151 (1986)] as probes. Additionally, flow cytometric detection of hybridization to ribosomal RNA has been successful [See J. G. Bauman et al., *Cytometry* 9:515–524 (1988)] and detection of a high abundance mRNA; α-actin in L929 cells has been reported [See E. A. Timm, Jr., C. C. Stewart, *Biofeedback* 12, 363 (1992)].

In this application, we describe a technique which combines the sensitivity of in situ polymerase chain reaction and the specificity of nucleic acid hybridization with the rapid and quantitative single cell analytic capability of flow cytometry. Unlike in situ polymerase chain reaction techniques performed on cells adhered to slides, the solution based technique described in this application potentially allows for the multiparameter analysis of large numbers of cells by flow cytometry and further characterization following cell sorting. Using this technique, we have detected a single HIV-1 proviral sequence per cell in an HIV-1 positive cell line and HIV-1 proviral sequences in HIV-1 infected patients.

SUMMARY OF THE INVENTION

It is an object of this invention to provide a diagnostic method to assess the viral burden of patients infected with a virus such as HIV-1, aberrant genes/translocations related to malignancy and birth defects and of maternal/fetal exchange. These objects are accomplished by the methods described in this application.

The present invention provides a method of detecting amplified nucleic acid sequences in cells using flow cytometry. More specifically, this invention provides a method to detect specific preselected nucleic acid sequences in cells by fluoresence activated cytometry involving the steps of a) isolating a class of cells; b) incubating the cells in a water soluble fixative to stabilize cells in suspension; c) amplifying specific nucleic acid sequences within cells in the presence of deoxyribonucleoside triphosphates coupled to molecules that prevent diffusion of amplified product from the cells; d) contacting the suspension of cells containing amplified nucleic acids with labeled nucleic acid probes complementary to the specific amplified nucleic acid sequence and e) detecting the labeled nucleic acid probes by fluoresence activated flow cytometry so to identify cells containing said preselected nucleic acid sequences. Both DNA and RNA nucleic acid sequences can be detected.

Still more specifically this invention provides a method to detect HIV-1 proviral DNA, RNA and mRNA in peripheral mononuclear cells by fluorescence activated flow cytometry by a) isolating peripheral blood mononuclear cells; b) incubating the peripheral blood mononuclear cells with a water soluble fixative to form a suspension; c) amplifying specific DNA sequences in the suspension of peripheral blood mononuclear cells in the presence of deoxyribonucleoside triphosphates coupled to molecules that prevent diffusion of amplified product from the cells; d) contacting the solution of peripheral mononuclear cells containing amplified proviral HIV-1 DNA with labeled nucleic acid probes complementary to the proviral HIV-1 DNA sequence; and e) detecting the labeled nucleic acid probes by fluoresence activated flow cytometry so to identify cells containing said HIV-1 proviral DNA. Similarly, this method can be practiced to detect HIV-1 mRNA sequences.

In these methods, the nucleic acid is retained in the cells using the water soluble fixative STF® (Streck Laboratories) and also by coupling certain deoxyribonucleoside triphosphates to large molecules such as steroids. More specifically, this invention provides the steroid digoxigenin coupled to the deoxyribonucleoside triphosphate UTP.

BRIEF DESCRIPTING FIGURES

The file of this patent contains at least one drawing executed in color. Copies of this patent with color drawing (s) will be provided by the Patent and Trademark office upon request and payment of necessary fee.

FIG. 1. Shows in situ PCR using primers SK38/39 on 8E5/LAV cells diluted to 50% using seronegative peripheral mononuclear cells. Amplificate remains in positive cells (dark brown) and negative cells contain no amplified product (light green). Color development was achieved using an alkaline phosphatase conjugated anti-digoxigenin antibody which binds to digoxigenin incorporated in the amplificate. The substrate NBT (nitro blue tetrazolium) xphosphate precipitates to form a brown product. Cells were counterstained with Fast Green.

FIG. 2. Standard curve of 8E5/LAV cells (HIV-1 positive) diluted with seronegative peripheral mononucleic cells as determined by in situ PCR and flow cytometric analysis (y-axis).

FIG. 3. Fluorescence histogram showing HIV-1 positive and HIV-1 negative cells quantitated by in situ PCR and flow cytometric analysis.

DETAILED DESCRIPTION OF THE INVENTION AND BEST MODE

Figure 1:
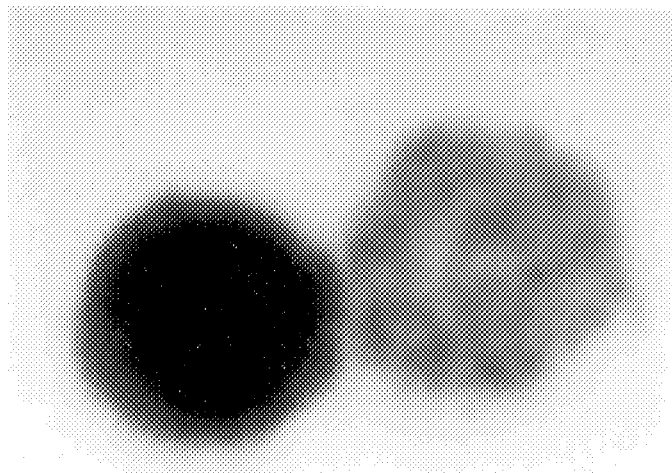

In accordance with the present invention amplified nucleic acid sequences in cells are detected using flow cytometry. When working with a flow cytometer, generally a specific class of cells are transported through the instrument. This invention specifically relates to the detection of certain preselected nucleic acid sequences in peripheral blood mononuclear cells, but other classes of cells such as monocytes, thymocytes and digested tissues can also be used.

The isolated cells are adjusted to a desired concentration for amplification such as $1\times10^6$ cells/ml. The cells are treated with a water soluble fixative, "STF"® (Streck Laboratories). "STF"® is a proprietary fixative agent containing acetic acid and zinc. The dilution that we found to be useful for pheripheral blood mononuclear cells was about the same as recommended for general tissue staining, i.e., about 1.5x, although, the correct concentration must be determined empirically for each type of cell examined. In order to assess concentration of the fixative agent both the morphology of the cell and the efficacy of amplification are reviewed.

In the context of this invention we will discuss amplification in terms of the polymerase chain reaction (PCR) technique (U.S. Pat. Nos. 4,683,202 and 4,683,195 hereby incorporated by reference), but it should be noted that other amplification techniques may also be used to practice this invention. See e.g. Erlich et al. EP 0 237 362, Dettagupta et al. EP 0 297 379, Becker EP 0 300 769, Burg et al. 0 310 229, Collins EP 0 328 822, Davey 0 329 822, Loewy et al. EP 0 369 775, EP 0 371 437, Gingeras EP 0 373 960, and Rose et al. EP 0 379 639.

The polymerase chain reaction amplification procedure was conducted as disclosed in U.S. Pat. No. 4,683,202 and 4,683,195. To facilitate retaining amplified product within the cell after application of proteinase K and thermal cycling, deoxyribonucleoside triphosphates are coupled to bulky molecules such as biotin or digoxigenin. We have found that the incorporation of these molecules during amplification provides a way to detect amplified DNA in a cell in solution because these molecules function to prevent amplified product from leaking out of the cell.

Amplification localization and optimization of cycling parameters were evaluated using an antibody to the compound coupled to the deoxyribonucleoside triphosphates. In particular, for detection of HIV-1-DNA certain primers SK38/39 (GAG) and SK68/69 (ENV) (primers available from Synthetic Genetics, San Diego, Calif.) provides the greatest sensitivity and specificity. Additionally, the concentration of magnesium also affected sensitivity and specificity. (Table 1)

This technique can be used to detect specific nucleic acid sequences such as HIV-1 proviral DNA, HIV-1 RNA, HLA-DQα, and potentially T-cell receptor and B-cell gene rearrangements.

EXAMPLE 1

HIV-1 Proviral DNA

Cell Lines and Viruses: 8E5/LAV cells are an established cell line containing a single copy of HIV-1 proviral DNA. 8E5/LAV is available from ERC Bioservices Corporation—catalog number 95. This reagent was obtained through the AIDS Research End Reference Reagent Program, Division of AIDS, NIAID, NIHS 8E5/LAV from Dr. Thomas (Folks. Folks, T. M. Powell, D., Lightfoote, M. Koenig, S., Fauci, A. S., Benn, S., Rabson A., Daugherty, D., Gendelman, H. E., Hoggan, M. D., Venkatesan, S., and Martin, M. A., Biological and biochemical characterization of a cloned Leu-3-cell surviving infection with the acquired immune deficiency syndrome retrovirus. *J. Exp. Med.* 164: 280–290, 1986.) The growth characteristics are provided in a data sheet that accompanies a shipment of the cell line.

8E5/LAV, an established cell line having one HIV-1 proviral DNA molecule per cell, was used to prepare a copy number standard curve for polymerase chain reaction amplification. Low passaged 8E5/LAV cells are maintained in suspension culture in RPMI 1640 media (Gibco Laboratories) supplemented with 20% fetal bovine serum (Hyclone Labs), 2 mM L-glutamine, penicillin (100 units/ml) and streptomycin (100 micrograms) in a humidified incubation with a 5% $CO_2$ atmosphere.

HIV-1 negative peripheral mononuclear cells were separated from the whole blood of normal healthy donors who were in a low risk for AIDS and who had been screened as negative for HIV-1 antigen/antibody and for Hepatitis B surface antigen. Mononuclear cells were separated from heparinsized whole blood by centrifugation on a LYMPHOCYTE SEPARATOR™ medium (Organon Teknike Corporation) gradient. The layer containing the peripheral mononuclear cells was removed and washed three times with Dulbecco's phosphate buffered saline, magnesium and calcium free (D-PBS, Gibco Laboratories) Cell suspensions of the positive control cells, 8E5/LAV, negative cells, and HIV-1 positive clinical samples were quantified by hemocytometer counting until duplicate counts were within 5% of each other. The concentration of cell suspensions was adjusted to $1 \times 10^6$ cells per milliliter with D-PBS. Four hundred microliters of this suspension is equivalent to 400,000 cells and in the case of 8E5/LAV cells is equivalent to 400,000 copy numbers of HIV-1 proviral DNA. Standard of curve dilution medium consisted of the HIV-1 negative peripheral blood mononuclear cells ($1 \times 10^6$ cells/milliliter) D-PBS. Several dilutions of 8E5/LAV cells were made in the standard curve dilution medium of negative peripheral mononuclear cells to obtain standard curve point of 50,000, 100,000, 200,000, and 400,000 copy numbers. The zero copy number point was HIV-1 negative peripheral mononuclear cells alone. Using a dilution medium of negative peripheral blood mononuclear cells ensured a consistent total number of cells in each polymerase chain reaction amplification tube. Four hundred microliters of each standard curve dilution and clinical sample was aliquoted in 0.5 ml microfuge tube (Eppendorf) for in situ polymerase chain reaction.

Peripheral blood mononuclear cells were isolated from fresh heparinezed blood layered on a HISTOPAQUE® 077 (Sigma, St. Louis, Mo.) density gradient. This gradient was centrifuged for 30 min. in GH-37 rotor at 1600 rpm at room temperature. The turbid mononuclear layer was removed and transferred to clean 15 ml. conical tube. The cells were washed twice with three volumes of RPMI and once with phosphate buffered saline (pH 7.6).

In situ Polymerase Chain Reaction: cell samples were adjusted to a concentration of $1 \times 106$ cells/ml and 400 µl of each sample was pelleted at 1500 rpm for two min. After removal of the supernatant, the cells were resuspended in 50 µl of "STF"® (Streck Laboratories, Omaha, Neb.) fixative and incubated at room temperature for fifteen min. Cells were again pelleted at 1500 rpm for two min. resuspended in 25 µl of 1 µg/ml proteinase K in 0.1M Tris HCL, 50 mM EDTA (pH 8.0), and incubated at 37° C. for fifteen min. Cells were pelleted as above, washed with phosphate buffered saline (pH 7.4) and placed on ice. 190 µl of polymerase chain reaction mixture (10 mM Tris HCL pH 8.3, 50 mM KCL, 1.5 mM MgCl, 0.25 mM dATP, dCTP, dGTP, 0.14 mM dTTP, 4.3 µM dUTP-11-digoxigenin ("GENIUS"™ 1 DNA labeling and Detection Kit, 100 pmole each forward and reverse primer (SK 38/39 Primers) 1.0 µl (5µ) Taq polymerase (AMPLITAQ®, Perkin Elmer, Norwalk, Conn.) and gelatin 0.001% w/v was added to said sample. (Samples were placed in a Perkin Elmer Cetus automated thermocycler once block temperature reached 80° C., then cycled. Thermal cycling parameters (optimal) were as follows: denaturation-94° C., one min., reannealing 58° C., two min., extension-74° C. 1.5 min. with five sec. added for each successive extension cycle. Cells were cycled for 40 cycles and stored at 4° C. after cycling if necessary. Amplification localization and optimization of cycling parameters were evaluated using an antidigoxigenin alkaline phosphatase conjugated antibody. See FIG. 1 and Table 1. Briefly, amplified cells were cytospun onto poly-L-lysine coated slides, washed with phosphate buffered saline pH 7.4 and incubated with the conjugated antibody for two hours at 37° C. Cells were washed as above and incubated with substrate (NBT/X-phosphate) for 10 min. at room temperature. Cells were counterstained with fast green (Rowley Biochemical Institute, Rowley, Mass.) and coverslipped.

TABLE 1

OPTIMIZATION OF IN SITU PCR CYCLING CONDITIONS USING IMMUNOHISTOCHEMICAL DEVELOPMENT

| PRIMERS | [Mg] | Sensitivity | Specificity |
|---------|------|-------------|-------------|
| GAG | 1.5 mM | 100% | 98% |
| (SK38/39) | 2.25 mM | 100% | 95% |
| ENV | 1.5 mM | 98% | 94% |
| (SK68/69) | 2.25 mM | 100% | 91% |

Solution hybridization. Sequence specific oligonucleotide probes (Applied Biosystems, San Diego, Calif.) SK19-FITC) containing multiple fluorescence tagged nucleotides were added to the polymerase chain reaction tubes (400 pmol/tube) along with 10 µg/ml sonicated herring sperm DNA. Tubes were heated to 94° C. for two min. and hybridization was performed for two hrs. at 560° C. Cells were washed under high stringency for thirty min. with 2× SSC/50% formamide/500 µg/ml bovine serum albumin at 420° C., 30 minutes with 1× SSC/50% formamide/500 µg/ml bovine serum albumin at 42° C., thirty min. with 1× SSC/500 µg/ml bovine serum albumin at room temperature, and briefly with phosphate buffered saline temperature. Cells were resuspended in phosphate buffered saline pH 8.3 and counterstained for flow cytometric analysis with 1 µg/ml propidium iodide.

Figure 2:
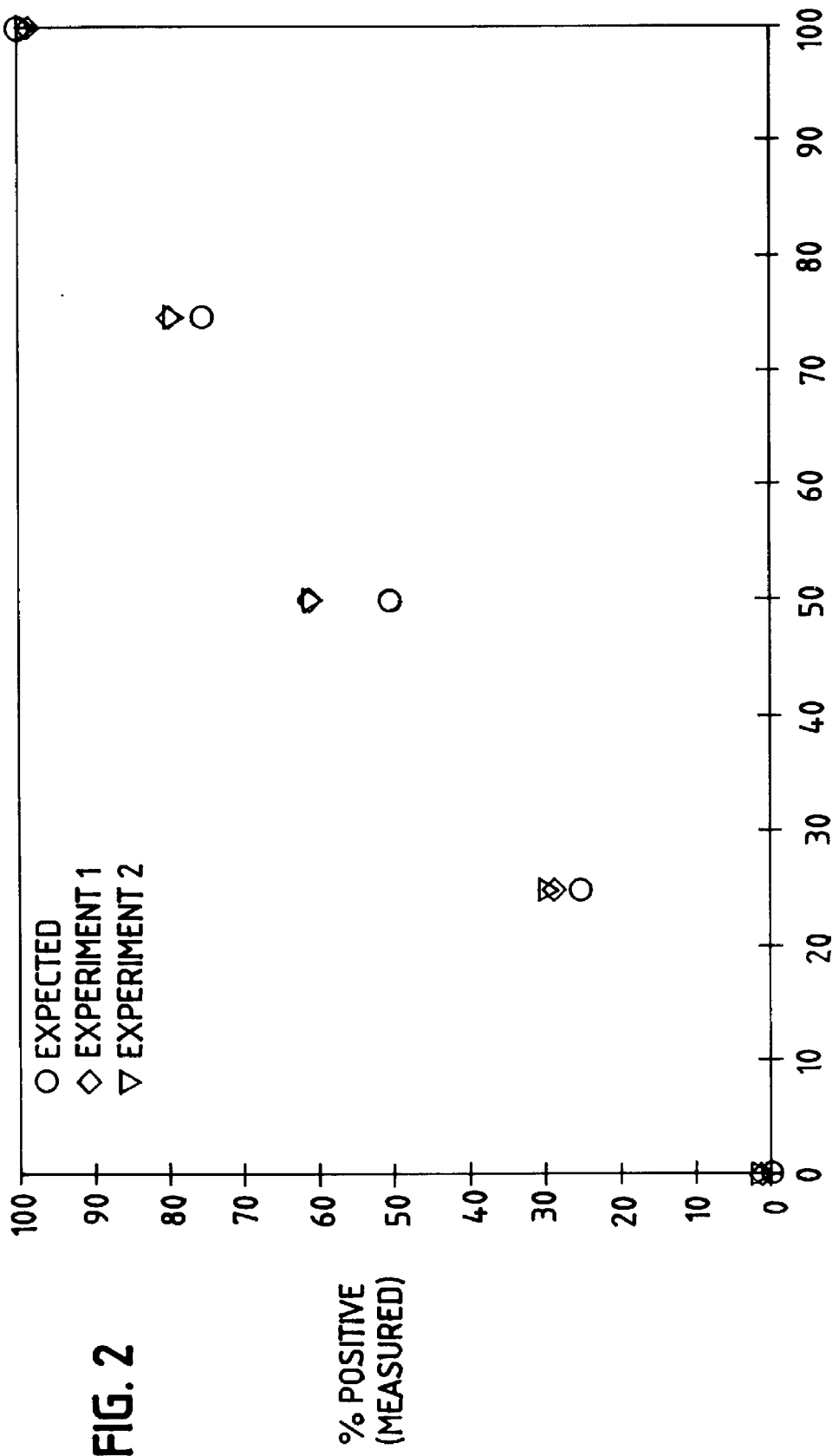
Figure 3:
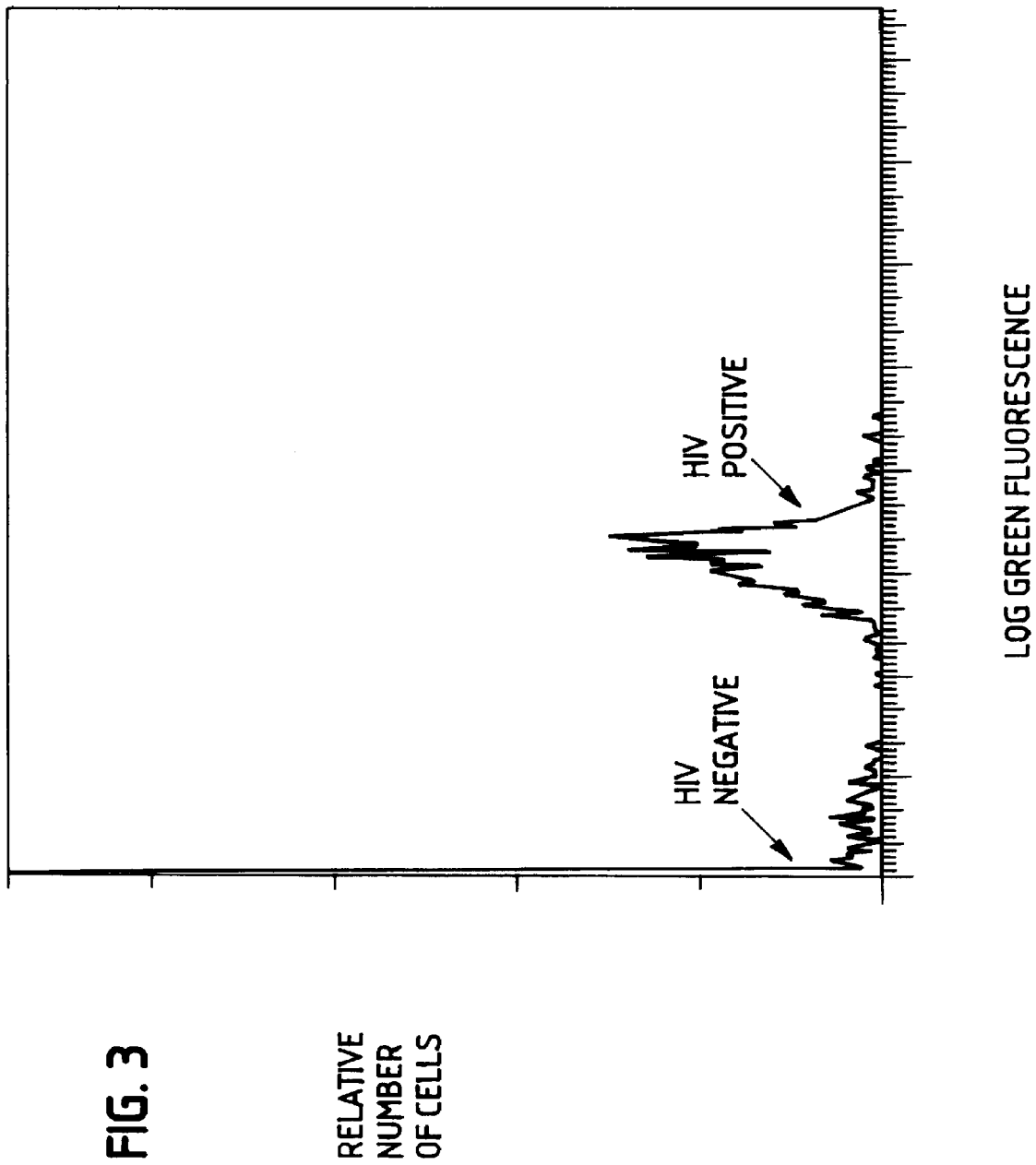

Flow cytometric analysis. All samples were filtered through a 7 µm nylon mesh just prior to analysis. Samples were analyzed on the Coulter Electronica "PROFILE II"™ flow cytometer with "POWERPAK"™ option (Coulter Electronica, Inc., Hialeah, Fla.) at Veterans Lakesize Medical Center. Laser excitation was 15 mW at 488 nm and the standard optical filter configuration was utilized for fluorescence light detection (488 nm dichroic, 457–502 nm long pass laser blocking, 550 nm dichroic, 525 band-pass FITC fluorescence), 600 nm dichroic, and 635 nm band-pass (propidium iodide fluorescence filter). Instrument sensitivity was standardized before each experiment employing "IMMUNO-BRIGHT"™ calibration beads (Coulter Source, Marriette, Ga.). Color compensation circuitry was adjusted using FITC only, PI only, and dual stained 100% HIV-1-positive cell samples. Standard curve showing the linearity of this assay is shown in FIG. 2. Sensitivity and specificity of this technique using the solution hybridization was 99.6% and 99.2% respectively (FIG. 3).

Three-Color Analysis of Cell Surface Markers. Monoclonal antibodies OKT4-FITC (Ortho diagnostics), CD3-

PerCP (Coulter Diagnostics), and CD2-PE (Coulter Diagnostics) were employed for cell surface phenotyping. Peripheral blood mononuclear cells were resuspended in 100 μl phosphate buffered saline (pH 7.4) and all antibodies were added at concentration recommended by the manufacturer. After thirty minutes incubation at room temperature the cells were fixed in 1% paraformaldehyde and analyzed by flow cytometry. The results of this analysis is shown in Table 2.

TABLE 2

In Situ PCR for HIV-1 Proviral DNA
Correlation with CD4 Counts

| Patient Number | CD4 (% of PBMC) | HIV-1 DNA+ (% of PBMC) |
|---|---|---|
| 1 | 14.3 | 15.0 |
| 2 | 28.3 | 3.2 |
| 3 | 35.2 | 1.4 |
| 4 | 0.1 | 4.2 |
| 5 | 0.2 | 0.0 |

The data presented in this table shows the detection of HIV-1 proviral sequences in HIV-1 infected patients. Patient No. 1 has symptoms of the disease and shows about 14% of the mononuclear cells being CD4+T-cells. Similarly, 15% of the mononuclear cells contain a HIV-1 proviral sequence. Patient No. 2 and 3 are asymptomatic and have higher T-cells percentages and lower HIV-1 proviral DNA percentages. Patients 4 and 5 are near death and show low T-cells and HIV-1 proviral DNA percentage. All patients are HIV-1 antibody positive.

EXAMPLE 2
In Situ RNA PCR

Lymphocytes were aliquoted and treated with fixative and proteinase K as described for DNA PCR, although all solutions were prepared with 0.1% Diethyl pyrocarbonate (DEPC) treated analytical reagent water (Mallinckrodt). Glassware and plasticware were used also treated with 0.1% DEPC prior to autoclaving.

To each 400,000 cell sample, 40 μl of reaction mixture for reverse transcription was added (10.0 units thermostable rTth DNA Polymerase (Perkin Elmer Cetus) 90 mM KCl, 100 mM Tris-HCl pH 8.3, 1.0 mM MnCl, 2, 200 μM each dGTP, dATP, dCTP, 125 μM dTTP, 4 μM dUTP-11-digoxigenin (Beorhinger Manheim), RNase Inhibitor 40 units (Perkin Elmer Cetus), 100 pmoles downstream primer. Samples were incubated for 15 minutes at 70° C. and placed on ice.

160 μl of PCR reaction mixture was then added (100 mMKCl, 10 mm Tris-HCl pH 8.3, 0.75 mM EGTA, 0.05% Tween 20, 5.0% (v/v) glycerol (Chelating buffer-Perkin Elmer Cetus) 2 mM MgCl2, 100 pmoles upstream primer. Samples were taken from ice and placed in an automated thermal cylcer with block temperature at 80° C. Cycling was then performed as previously described.

The primers used for RNA amplification (MF111, MF126) were provided by Dr. M. Furtado. 5869–5886 MF111 GCGAATTCATGGAGTCCAGTAGATCCTA-GACTA (Sequence Id. No. 1(G) and 2(T)) 8760–8733 MF126 GCTCTAGACTATCTGTCCCCTCAGC-TACTGCTATGG (Sequence Id. No. 3) flank a major splice site within the mRNA species which encodes the TAT protein.

Solution hybridization was then performed as described for DNA with a fluorescently labeled oligonucleotide probe which crosses the mRNA splice site (MFA-1) MFA-1 TTCTCTATCAAAGCAACCCACCTCCCAATC (Sequence Id. No. 4).

Cells used as positive controls were CEM cells infected with NL4-3 HIV-1.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. A method to detect specific nucleic acid target sequences in a cell lacking a cell wall by fluorescence-activated cytometry comprising:
   (a) isolating cells lacking a cell wall;
   (b) incubating said cells with a water-soluble fixative to form a suspension;
   (c) washing the cells;
   (d) amplifying specific target nucleic acid sequences in said washed cells in the presence of deoxyribonucleoside triphosphate analogs wherein said analogs are deoxyribonucleoside triphosphates coupled to a substituent group that inhibits cellular effusion of amplified target nucleic acid products containing said analogs;
   (e) contacting said suspension of cells containing amplified target nucleic acids with labeled nucleic acid probes sufficiently complementary to said target nucleic acid sequences so as to specifically bind to them; and
   (f) detecting said labeled nucleic acid probes by fluorescence-activated flow cytometry so as to identify cells containing said nucleic acid target sequences.

2. The method of claim 1 wherein said specific nucleic acid target sequence is HIV-1 DNA.

3. The method of claim 1 wherein said nucleic acid target sequence is DNA.

4. The method of claim 1 wherein said nucleic acid target sequence is RNA.

5. The method of claim 1 wherein said specific nucleic acid target sequence is HIV-1 RNA.

6. The method of claim 1 wherein said cells are peripheral mononuclear cells.

7. The method of claim 1 wherein said deoxyribonucleoside triphosphate analog is dUTP.

8. The method of claim 1 wherein said subtituent is digoxigenin.

9. A method to detect HIV-1 DNA target sequences in peripheral mononuclear cells by fluorescence-activated flow cytometry comprising:
   (a) isolating said peripheral mononuclear cells;
   (b) incubating said peripheral mononuclear cells with a water-soluble fixative to form a suspension;
   (c) washing the cells;
   (d) amplifying said HIV-1 DNA target sequences in said washed cells in the presence of deoxyribonucleoside triphosphate analogs wherein said analogs are deoxyribonucleoside triphosphates coupled to a substituent that inhibits cellular effusion of amplified products containing said analogs;
   (e) contacting said suspension of cells containing amplified HIV-1 DNA target sequences with labeled nucleic acid probes sufficiently complementary to said HIV-1 DNA target sequences so as to specifically bind to them; and
   (f) detecting said labeled nucleic acid probes by fluorescence-activated flow cytometry so as to identify cells containing said HIV-1 DNA target sequences.

10. The method of claim 9 wherein said fixative agent is a water soluble fixative.

11. The method of claim 9 wherein said deoxynucleotide triphosphate is dUTP.

12. A method according to claim 9 wherein said substituent group is digoxigenin.

13. A method to detect HIV-1 RNA target sequences in peripheral mononuclear cells by fluorescence-activated flow cytometry comprising:

(a) isolating said peripheral mononuclear cells;
(b) incubating said peripheral mononuclear cells with a water soluble water-soluble fixative to form a suspension;
(c) washing said cells;
(d) amplifying said HIV-1 RNA target sequences in said washed cells in the presence of deoxyribonucleoside triphosphate analogs wherein said analogs are deoxyribonucleoside triphosphates coupled to a substituent that inhibits cellular effusion of amplified products containing said analogs;
(e) contacting said suspension of cells containing amplified HIV-1 RNA target sequences with labeled nucleic acid probes sufficiently complementary to said HIV-1 RNA target sequences so as to specifically bind to them; and
(f) detecting said labeled nucleic acid probes by fluorescence-activated flow cytometry so as to identify cells containing said HIV-1 RNA target sequences.

14. The method of claim 13 wherein said fixative agent is is a water soluble fixative.

15. The method of claim 13 wherein said substituent group is digoxigenin.

16. The method of claim 15 wherein said deoxynucleoside triphosphate is dUTP.

* * * * *

UNITED STATES PATENT AND TRADEMARK OFFICE
CERTIFICATE OF CORRECTION

PATENT NO. : 5,840,478
DATED : November 24, 1998
INVENTOR(S) : Patterson, Bruce; Till, Michelle; Wolinsky, Steven It is certified that errors appear in the above-identified patent and that said Letters Patent is hereby corrected as shown below:

On the title page, item [56] References Cited, under Other Publications

Column 2, line 7: "Albumith" should read --Albumin--

Column 2, line 21: "Nucei" should read --Nuclei--

In Column 5, line 67: --(hereby incorporated by reference)-- should be inserted after "Kit"

In Column 6, line 19: "fast green" should read --Fast Green--

In Column 8, lines 17-18: "GCGAATTCATGGAGTCCAGTAGATCCTAGACTA" should read -- GCGAATTCATGGAG/TCCAGTAGATCCTAGACTA --

Signed and Sealed this

Twenty-sixth Day of October, 1999

Q. TODD DICKINSON

*Attest:*

*Attesting Officer*　　*Acting Commissioner of Patents and Trademarks*